United States Patent [19]

Koenig et al.

[11] Patent Number: 4,502,951

[45] Date of Patent: Mar. 5, 1985

[54] SUCTION DEVICE FOR OBTAINING DUST SAMPLES

[75] Inventors: Rainer Koenig, Eschborn; Rolf Sieglen, Sulzbach; Wolfgang Weisser, Bad Homburg von der Hohe; Helga Heide, Kelkheim, all of Fed. Rep. of Germany

[73] Assignee: Luossavaara-Kiirunavaara AB, Stockholm, Sweden

[21] Appl. No.: 451,948

[22] Filed: Dec. 21, 1982

Related U.S. Application Data

[62] Division of Ser. No. 225,199, Jan. 15, 1981, Pat. No. 4,482,864.

[30] Foreign Application Priority Data

Jan. 18, 1980 [DE] Fed. Rep. of Germany ....... 3001704

[51] Int. Cl.³ .................................................. B07B 7/06
[52] U.S. Cl. ........................................ 209/21; 209/30; 209/143; 209/250; 209/243; 55/482; 55/468; 73/863.23; 73/864.33; 73/864.41
[58] Field of Search ............. 209/250, 235, 236, 252, 209/253, 143, 243, 262, 263, 153, 22-36, 906, 21; 406/121, 171; 15/378, 422; 55/482, 468, 69, 71, 52, 152, 141; 73/863.23, 863.21, 864.33, 864.41

[56] References Cited

U.S. PATENT DOCUMENTS

| | | | |
|---|---|---|---|
| 554,043 | 8/1895 | Landis | 209/153 |
| 759,151 | 5/1904 | Benefield | 209/250 |
| 1,209,911 | 12/1916 | Wagner | 55/482 |
| 1,355,507 | 10/1920 | Roever | 209/250 |
| 1,961,921 | 6/1934 | Bowen | 209/250 |
| 1,994,869 | 3/1935 | Replogle | 15/422 |
| 2,531,920 | 11/1950 | Raminger | 15/422 |
| 3,137,543 | 6/1964 | Barton et al. | 23/230 |
| 3,384,233 | 6/1968 | Bolles | 209/153 |
| 3,426,510 | 2/1969 | Schaaf | 209/250 |
| 3,662,886 | 5/1972 | Kennedy | 209/250 |
| 3,686,563 | 8/1972 | Walter | 324/13 |
| 3,704,482 | 12/1972 | Brannon | 406/69 |
| 3,804,245 | 4/1974 | Pendleton | 209/250 |
| 3,808,524 | 4/1974 | Tarassoff et al. | 324/34 R |
| 3,843,198 | 10/1974 | Reynolds | 299/18 |

FOREIGN PATENT DOCUMENTS

| | | | |
|---|---|---|---|
| 178760 | 11/1906 | Fed. Rep. of Germany | 15/378 |
| 53954 | 4/1969 | Luxembourg . | |
| 1898 | of 1874 | United Kingdom | 209/153 |
| 599613 | 3/1948 | United Kingdom . | |

Primary Examiner—Frank W. Lutter
Assistant Examiner—William Bond
Attorney, Agent, or Firm—Fisher, Christen & Sabol

[57] ABSTRACT

Suction device for obtaining dust samples of nearly homogeneous grain sizes and with a reproducible bulk density for the analysis of ores. The device, which is suitable for use during the mining of ores, includes a cylindrical casing, having an opening at each end thereof, and a cylindrical sieve insert, having an opening at each end thereof and being coaxially located within the casing. An inwardly-facing conically-shaped insert, located at the front end of said casing, provides flow communication between the front end of the casing and the sieve insert. A suction pipe socket is located laterally on the casing for attachment to suction-generating equipment. A filter is located over the mouth of the conically-shaped insert. The front end of a downwardly-curved dust-conducting tube is in direct communication with the back end of the sieve insert. There is a tube for collecting samples from the dust-conducting tube. The nozzle-like taper of the conically-shaped insert accelerates the dust particles which have been drawn into the device and have passed through the filter. The smaller dust particles, following the deflection of the air flow caused by the lateral suction through the suction pipe socket pass through the sieve insert and out the suction pipe socket. The larger dust particles, not being deflected by the lateral suction, pass through the dust-conducting tube into the sample container.

2 Claims, 4 Drawing Figures

Fig—2

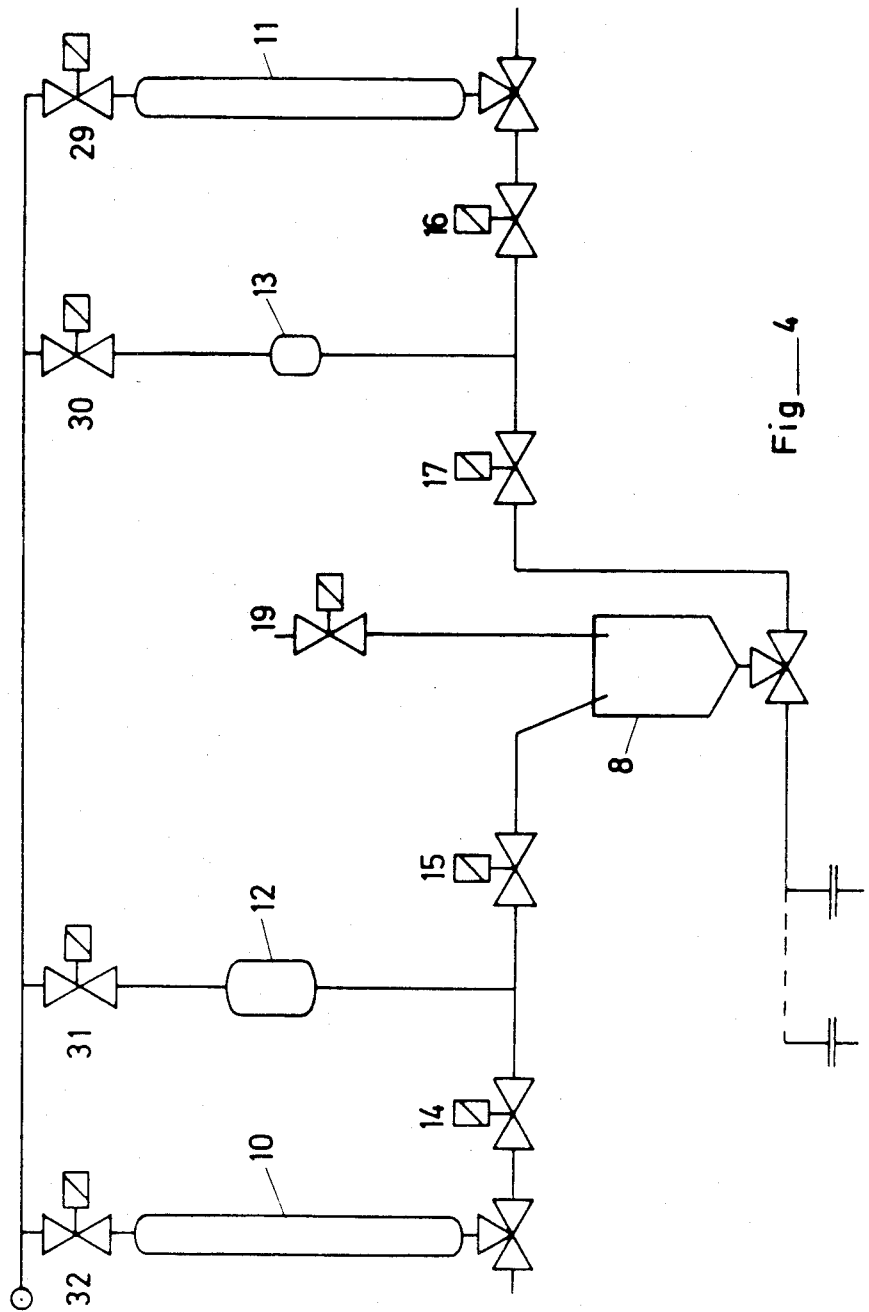
Fig.__4

SUCTION DEVICE FOR OBTAINING DUST SAMPLES

This is a division of application Ser. No. 225,199, filed Jan. 15, 1981, now U.S. Pat. No. 4,482,864.

BACKGROUND OF THIS INVENTION

1. Field of this Invention

This invention relates to a process and equipment for the determination of the magnetite and phosphorus contents in magnetite-containing ores, either during the mining or processing of the ores.

2. Prior Art

During the mining of mineral raw materials, the composition of the raw materials must be continuously checked. This permits the determination of the percentages of gangue and ore and is often also necessary in order to minimize the content of specific undesired admixtures. Usually random samples of the raw material are taken by means of a shovel or gripping tools. The samples are then prepared for chemical analysis, e.g., they are ground and homogenized. The analysis has to be carried out so rapidly that it is thereby possible to intervene in the handling of the materials or the processing according to the result of the analysis.

As the analysis, including the sampling and processing of the sample, takes a relatively long period of time, it has so far only been possible to take samples and to intervene in the process according to the results of the analysis after much too long intervals of time. In the case of the underground mining of iron ore in a large mine, for example, this results in undesired mixing of ores having different phosphorus contents. The results of such mixing process is that the yield of ore having low phosphorus content is substantially below the theoretical yield. Mixing occurs during the actual mining process. The blasted ore is transported by bucket loaders to shafts about 40 to 200 m away. One bucket holds about 8 to 14 tons. A sample of about 1 kg is taken only from approximately every tenth bucket by means of a gripping tool. Such sample is ground, sifted and magnetically separated. Part of such sample is dried, and part of this latter amount is measured, removed and subjected to wet chemical analysis. On the basis of the result of such analysis, all further buckets handled (until the result of the next analysis is available) are tipped into the shaft for the grade of ore determined by the analysis, although as a rule the composition of the material changes from bucket to bucket. The phosphorus content, which essentially determines the quality of the ore, may fluctuate by a factor of 10 to 100.

BROAD DESCRIPTION OF THIS INVENTION

The main objective of the present invention is to provide a process and equipment which make it possible to take representative samples of the ore material and to analyze them within a sufficiently short period of time for magnetite and phosphorus contents, the material being subsequently forwarded to analysis and sorting. By means of such a process a sample is to be taken from each bucket in the way described above and analyzed so rapidly that the bucket contents can be placed into the shaft for the respective composition or quality without any delay. Another object of this invention is to provide a process and equipment which can be used during the mining or processing of the ore. Other objects and advantages of this invention are set out herein or are obvious herefrom to one ordinarily skilled in the art.

The objects and advantages of this invention are achieved by the process and equipment of this invention.

It has been found that the objects of this invention can be achieved by a process in which a sample of dust, which has been produced artifically or obtained as byproduct, is collected and placed in an electromagnetic field, the magnetite content of the dust sample is determined from changes in the magnetic flux or the relative permeability, and the phosphorus content of the total dust sample mass is then determined. Preferably the total dust sample mass is also determined from changes in the magnetic flux or the relative permeability. This invention provides a process for the determination of the magnetic and phosphorus contents of magnetite-containing ores.

Preferably fractions of identical grain size (of the dust sample) are used for the determination of magnetite content. Also preferably the dust sample is dried prior to measuring the change in the magnetic flux or the relative permeability.

This invention also involves equipment for carrying out the process of this invention. The equipment has a coil system which includes at least one measuring coil for determining the magnetite content. The core of the measuring coil forms a tube, the minimum filling height of which exceeds the length of the coil.

Preferably the equipment has an additional measuring coil, which has a length that exceeds the maximum filling height of the tube, for determination of the sample mass. Preferably the coil system is designed according to the transducer principle and is provided with a primary coil in addition to the two measuring coils—the length of the primary coil exceeding the maximum filling height of the tube. Preferably the tube is connected to a reaction chamber for carrying out the phosphorus analysis, and the reaction chamber is connected to reagent storage containers. Also preferably dosing devices are provided between the reagent storage containers and the reaction chamber which consist of dosing chambers and corresponding valves, and preferably an excess pressure can be generated in the containers via the appropriate valves. Preferably a microprocessor is provided for evaluating the measured valves and simultaneously controlling the operation of the equipment. Preferably, in the dust collecting equipment, the tube is connected to a dust collecting unit, most preferably via an elbow. Preferably the elbow and/or tube are provided with a heating device.

This invention further involves dust collecting equipment designed as a suction device. The equipment is provided with a lateral suction pipe socket and a coaxial sieve insert. The front of the dust collecting unit is covered with a front filler. Preferably entrance of the central passageway of the equipment is tapered towards the inside. Preferably the length and diameter of the part of the suction device limited by the sieve insert and the mesh size of the coaxial sieve insert are adjusted in such a way that only particles that are larger than the mesh size reach the tube. Also, preferably a motor-driven circular brush is positioned in front of the equipment in such a way that the dust generated by the brush can be sucked into the equipment.

To obtain as representative of a sample material as possible, a dust collecting unit is used according to this invention which features in particular the following special design characteristics:

- Reduction of the fine dust fraction in favor of the coarse dust fraction in order to obtain a sample that can be easily poured and has reproducible bulk density; and
- Easy conveyance of the deposited coarse dust into a tube where the total mass of the dust sample and its magnetite content are determined.

DETAILED DESCRIPTION OF THIS INVENTION

The dust collecting unit is designed, for example, as a cylindrical suction device with a lateral suction pipe socket. The dust sample is first sucked in through a front filter with a mesh size of, e.g., 100 μm. The inside of the suction device is provided with a coaxial sieve of gauze filter insert. The length and diameter of the hollow cylinder formed by the filter insert and the mesh size of the filter insert are such that all of the particles that are larger than the mesh size of the filter reach the tube where the dust is collected, as they are not sufficiently decelerated and deflected because of their inertia. The smaller particles, on the other hand, are sucked off through the meshes of the sieve or filter insert. In addition, the front of the suction device is provided with a nozzle-type taper which accelerates the dust particles sucked in through the front filter to such an extent that the larger particles do not follow the deflection of the air flow achieved by the lateral suction.

The analytical equipment for determining the magnetite and phosphorus contents of the dust consists essentially of two main components: a magnetic coil unit for determining the magnetite content and the total sample mass and a unit for the wet-chemical analysis of phosphorus. The magnetic coil unit contains a tube into which the sample material is fed for analysis. The tube is surrounded by a coil system. If alternating voltage is applied to the coil system, a magnetic field is generated inside the coil. When the sample to be analyzed is introduced into the tube which forms the core of the coil, the magnetic flux or the relative permeability of the core changes as a function of the magnetite content of the sample. From this change both the filling height or the total sample mass and the magnetite content are determined.

If two coaxial coils are used, the coil whose length is smaller than the minimum filling height of the tube serves for measuring the magnetite content, and the second coil whose length exceeds the maximum filling height of the tube is used to measure the total dust sample mass.

If the coil system consists of three coils, one coil is used as a primary coil. Its length exceeds the maximum filling height of the tube containing the sample. At a given primary voltage $U_p$, the secondary voltage $U_1$ is a function of the magnetite content of the dust sample. In addition, the height of the magnetite-containing dust column can be determined from the ratio of the voltages $U_2/U_1$. The following relations apply:

$$C_V^M = F(U_1) \tag{I}$$

wherein $C_V^M$ is the volume percentage of magnetite. If the total sample mass is $M_D$, the following equation applies:

$$M_D = f(U_2)(1 - \gamma_W \gamma_M^{-1}) + (f(U_2))/(f(U_1)) \cdot \gamma_M^{-1} \cdot \gamma_W \tag{II}$$

wherein:

$$f(U_1) = k_2 U_1 + k_3 = C_V^M \tag{III}$$

$$f(U_2) = k_1 U_2/U_1 \text{ and} \tag{IV}$$

$$\Delta\gamma = \gamma_M - \gamma_W$$

wherein $\gamma_M$ is the specific gravity of magnetite and $\gamma_W$ is the specific gravity of the non-magnetite-containing part of the sample.

The total sample mass is:

$$M_D = \Delta\gamma \cdot k_1(k_2 U_2 + k_3 U_2/U_1) + \gamma_W \cdot k_1 U_2/U_1 \tag{V}$$

Exact determination of the magnetite content or the iron content requires a homogeneous and largely uniform grain size distribution in the dust sample and constant, low humidity of the sample, as differing bulk densities of the dust column have an adverse effect on the measuring accuracy.

The dust sample whose mass has been determined by means of the magnetic coil system is analyzed for phosphorus. The phosphorus content is measured photometrically by a known method, the sample being reacted with a molybdate vanadate reagent. The reagent/acid combination must be exactly dosed. Later, water introduction into the reaction chamber is effected through a special system of storage containers, dosing chambers and valves. On completion of the analysis, the measured values are evaluated in a microprocessor. This microprocessor can simultaneously control the operation of the equipment.

The main advantage of this invention may be regarded as the fact that sufficiently large amounts of dust can be made available for analysis. In addition, it permits exact measurement of different amounts of dust, which is a prerequisite for phosphorus analysis. Further advantages are that the equipment can be mounted on a loader and that it resists the high stresses occuring during the loading process. The equipment for the wet-chemical analysis of phosphorus is designed such that it has no moving mechanical parts apart from a few electrovalves; this ensures that it meets the requirements for a simple analytical set-up which is not sensitive to vibrations. The total time required for the analysis of magnetite and phosphorus is less than 60 sec. For special applications, the electronic components of the dust sampling equipment can likewise be mounted separately outside of the equipment, without impairing its proper functioning.

In the following description this invention is described in detail on the basis of the attached drawings, which illustrate one embodiment of this invention. In the drawings:

FIG. 4 is a schematic of the equipment for phosphorus analysis of one embodiment of this invention.

Figure 1:
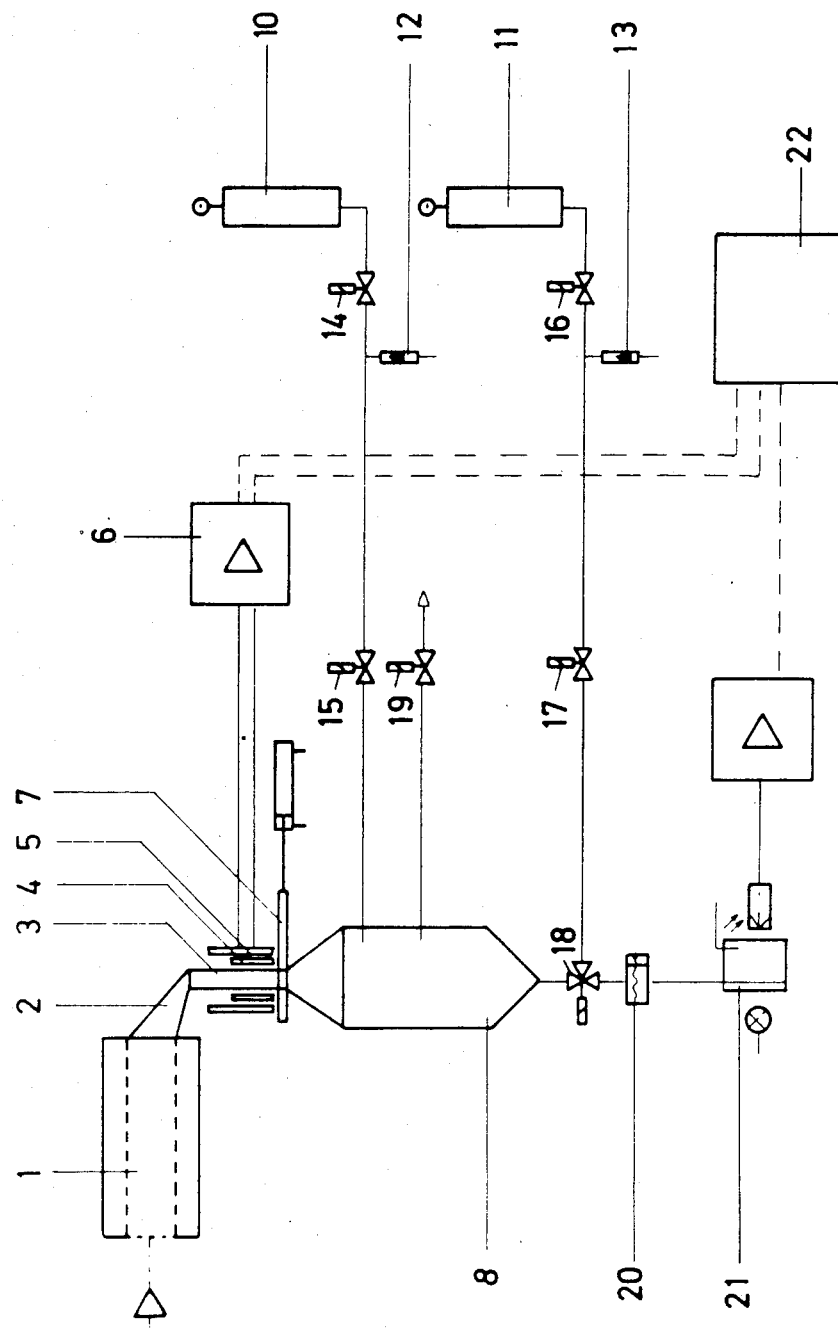
FIG. 1 is a schematic of the total dust sampling equipment of one embodiment of this invention.

FIG. 1 shows dust collecting unit 1 connected to tube 3 via elbow 2. In this embodiment, tube 3 is surrounded by two coils 4 and 5, which are electrically supplied from a.c. power source 6.

The samples collected by dust collecting unit 1 which consist of particles of a grain size range from 100 to 15 μm. preferably with a mean grain diameter of 65 μm, can be dried at about 100° C. by providing a heating device (which is not shown in the figure) at elbow 2 and/or at tube 3. The lengths of coils 4 and 5 and the filling height of tube 3 are such that coil 4 is shorter than the height of the dust column but coil 5 is longer than it. The exact filling height is measured by means of coil 5, while coil 4 serves for determining the magnetite content. The total sample mass is calculated from the values measured by coils 4 and 5.

After the magnetic measurement, which is completed within a few seconds, gate 7 is opened and the sample drops into reaction chamber 8. In this chamber the reaction of phosphorus with acid molybdate/vanadate reagent, which is necessary for photometric analysis, is initiated at about 90° C. Dosing of the acid/reagent combination and of the water for dilution is effected using storage containers 10 and 11, dosing chambers 12 and 13 and valves 14 to 18. By means of compressed air, which is introduced through valve 19, the liquid medium is thoroughly mixed with the dust and the phosphorus-containing component is thus rapidly dissolved. If the phosphorus compound is present, for example, in the form of apatite, the reaction is completed within 30 sec., provided that the acid/reagent combination is of optimum composition. Subsequently, the solution is transferred into a flow cell with photometer 21 through filter 20. The measured values are evaluated by means of microprocessor 22, which can simultaneously control the operation of the equipment.

Figure 2:
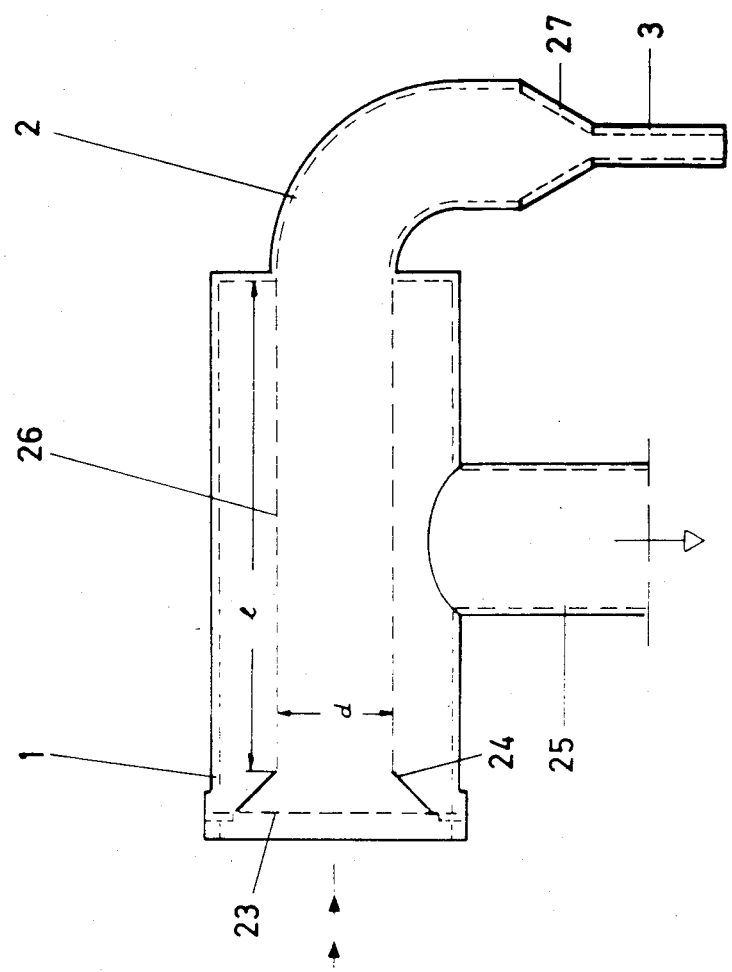
FIG. 2 is a cross-sectional view of the dust collecting unit of one embodiment of this invention.

FIG. 2 illustrates the principle of operation of the dust collecting unit according to this invention. The dust is sucked in through front filter 23, which can have a mesh size of about 100 μm. This ensures that only grain size fractions smaller than 100 μm reach suction device 1, which in this embodiment is a cylindrical tube. Conical taper 24 in the front part of the suction device causes a strong acceleration of the dust particles. Air is sucked off through lateral suction pipe socket 25. The inside of the suction device is provided with coaxial sieve or gauze filter insert 26. The flow resistance of this sieve insert ensures uniform pressure distribution within suction device 1. Length l and diameter d of the hollow cylinder formed by gauze filter 26, and the mesh size of the gauze filter are such that all particles which are larger than the mesh size reach elbow 2, as they are not sufficiently decelerated and deflected because of their inertia. The smaller particles, on the other hand, are sucked through the meshes of gauze filter 26. As a result, the gauze filter only becomes slightly polluted and there are long service-free periods. Dust particles which reach elbow 2 do not contain a fine grain fraction. The resultant sample material is therefore easy to pour and falls through funnel 27 into measuring tube 3. This process can be supported by a vibrator (which is not shown in the figure). In general, however, such a measure is not necessary as the manner in which the whole equipment is used, e.g., mounted on a loader, ensures sufficient vibration. Funnel 27 and tube 3 can also be connected direct to the casing of suction device 1 without using elbow 2.

Figure 3:
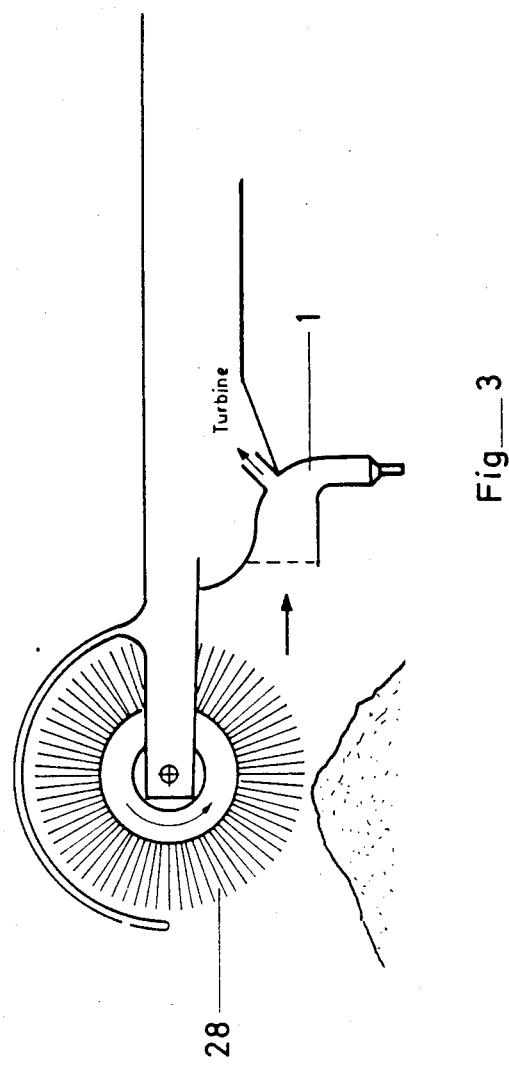
FIG. 3 is a partially cutaway side view of the equipment for one potential dust generating method of one embodiment of this invention.

FIG. 3 shows the principle of a device for dust generation. It consists essentially of motor-driven circular steel brush 28 and can be positioned in front of dust collecting unit 1 so that the particles can be sucked in by the dust collecting unit. Another possible means of artificial dust generation consists, for example, in the application of compressed air.

FIG. 4 illustrates the mode of operation of the equipment for the wet-chemical analysis of phosphorus. This embodiment features a two-stage process: the first stage involves the dosing of a mixture of nitric acid and molybdate/vanadate reagent, and in the second stage this mixture is diluted with water. It is, however, also possible to dose in only a mixture of nitric acid and molybdate/vanadate reagent without any further dilution with water. While valves 19 and 17 are open, dosing chamber 13 is first deaerated. Then valve 17 is closed, and valves 16 and 29 are opened. Storage container 11 is thus subjected to excess pressure, and liquid is fed from storage container 11 to dosing chamber 13 until a pressure corresponding to the excess pressure existing in storage container 11 is reached. After valve 16 has been closed, valve 17 and shortly afterwards valve 30 are opened, and liquid is transported into reaction chamber 8. Stirring is subsequently effected by means of the compressed air which is admitted through valve 19, dosing chamber 13 and valve 17. Dosing in of the water, which is supplied from storage container 10 to dosing chamber 12 and reaction chamber 8, is effected in an analogous manner by actuation of valves 14, 15, 31 and 32. After the closing of valve 19, reaction chamber 8 is subjected to excess pressure and the liquid from reaction chamber 8 is filtered off through filter 20 for subsequent photometric measurement.

What is claimed is:

1. Suction device for obtaining dust samples of nearly homogeneous grain sizes and with a reproducible bulk density for the analysis of ores, said device being suitable for use during the mining of ores, comprising:
   (a) a cylindrical casing, having a first end and a second end, and having an opening at said first end and an opening at said second end;
   (b) a cylindrical sieve insert, having an opening at each end thereof and being coaxially located within said casing;
   (c) an inwardly-facing conically-shaped insert provided at said first end of said casing, said conically-shaped insert providing flow communication between said first end of said casing and said sieve insert;
   (d) a suction pipe socket located laterally on said casing, said suction pipe socket adapted for attachment to suction means, and when said suction means is attached and operating, a suction is drawn in said cylindrical sieve insert, said conically-shaped insert and said first end of said casing, and through a filter;
   (e) said filter located over the mouth of said conically-shaped insert, said filter only allowing the passage of a gasious suspension of said dust;
   (f) a downwardly-curved dust-conducting tube, having a first end and a second end, and said first end thereof being in direct communication with the end of said sieve insert opposite to said first end of said casing;
   (g) a tube for a dust sample, which is in direct communication with said second end of said dust-conducting tube, whereby said dust is drawn into said first end of said casing and through said filter, said dust being composed of smaller particles and larger particles, said inwardly-facing conically-shaped insert accelerates said dust particles which have passed through said filter, said smaller particles of said dust following the deflection of the air flow caused by the lateral suction through said suction pipe socket, and the larger particles of said dust not being deflected by said lateral suction and passing through said dust-conducting tube into said sample tube.

2. The device as claimed in claim 1 wherein a motor-driven circular brush is positioned in front of said first end of said casing in such a way that the dust generated by the brush is sucked into said conically-shaped insert.

* * * * *